United States Patent [19]

Terwilliger et al.

[11] Patent Number: 5,146,921
[45] Date of Patent: Sep. 15, 1992

[54] BIOPSY INSTRUMENT STYLET AND CANNULA ASSEMBLY

[75] Inventors: Richard A. Terwilliger, Alamo; John D. Hebert, San Francisco; Jack Hall, Portola Valley, all of Calif.

[73] Assignee: Vance Products Inc., Spencer, Ind.

[21] Appl. No.: 583,597

[22] Filed: Sep. 17, 1990

Related U.S. Application Data

[63] Continuation-in-part of Ser. No. 521,259, May 9, 1990, Pat. No. 5,048,538, which is a continuation of Ser. No. 441,776, Nov. 27, 1987, Pat. No. 4,940,061.

[51] Int. Cl.$^5$ .............................................. A61B 10/00
[52] U.S. Cl. ..................................... 128/754; 606/171
[58] Field of Search ............... 128/749, 751, 754, 755; 606/167, 170, 171

[56] References Cited

U.S. PATENT DOCUMENTS 4,600,014  7/1986  Beraha ........................ 606/171

Primary Examiner—Randy C. Shay
Attorney, Agent, or Firm—Woodard, Emhardt, Naughton, Moriarty & McNett

[57] ABSTRACT

An instrument for removing tissue samples from a tissue mass which automatically penetrates, severs, and removes a tissue portion for examination. The instrument is motor powered, preferably by self-contained rechargeable batteries, and employs electrically actuated stops to control the action of penetration into and retraction from the tissue mass. The tissue penetrating means and severing means includes an inner stylet which penetrates the tissue mass and a hollow outer tube or cannula which surrounds the stylet and serves to sever a sample of tissue. In a preferred form the tissue penetrating end of the stylet is notched so that when the stylet penetrates the tissue mass, a portion of the tissue relaxes in the notched area. After tissue penetration by the stylet, the cannula, having a cutting surface at its distal end, penetrates the tissue and cuts off the tissue portion residing in the notched area of the stylet. The tissue penetrating and severing means are operably connected to a motor powered rotary cam assembly by means of cam followers and the rotary motion of the cam is converted to sequential, linear motion in the tissue penetrating means and severing means. The stylet mount and the cannula mount each have a recess in the backside thereof to receive a respective drive rod. A locking mechanism, such as annular grooves on the drive rods engage radially inward projections in the recess of the mounts to secure the mounts to the drive rods. A lever mechanism is provided to urge the mounts off of the drive rods for removal.

20 Claims, 17 Drawing Sheets

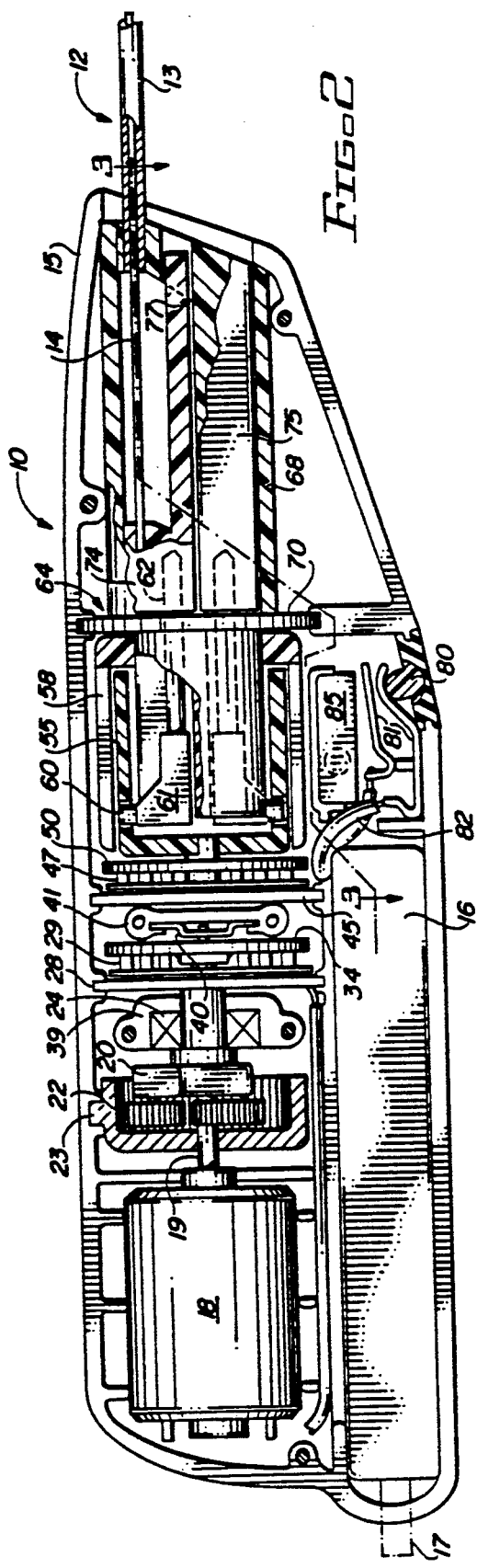

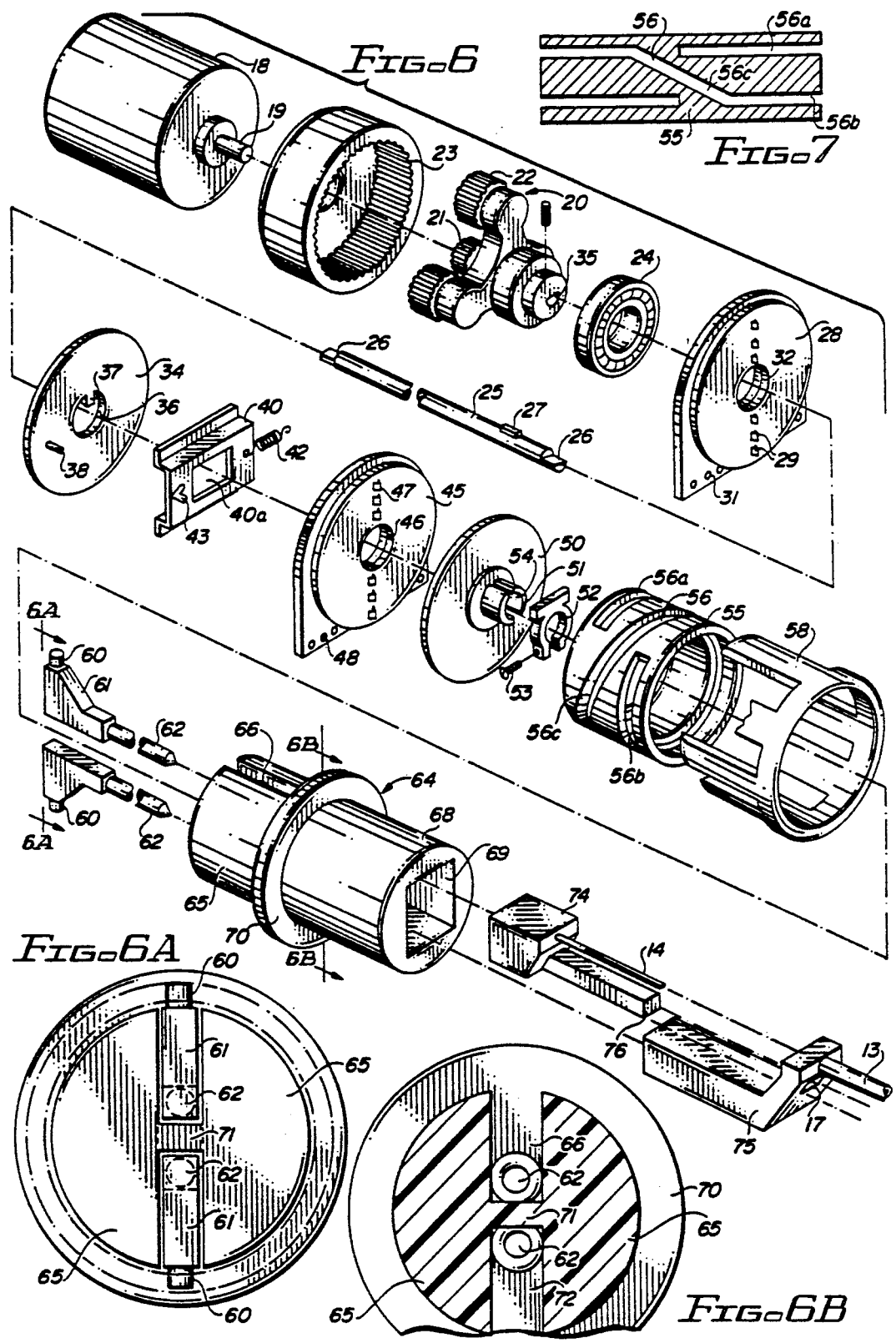

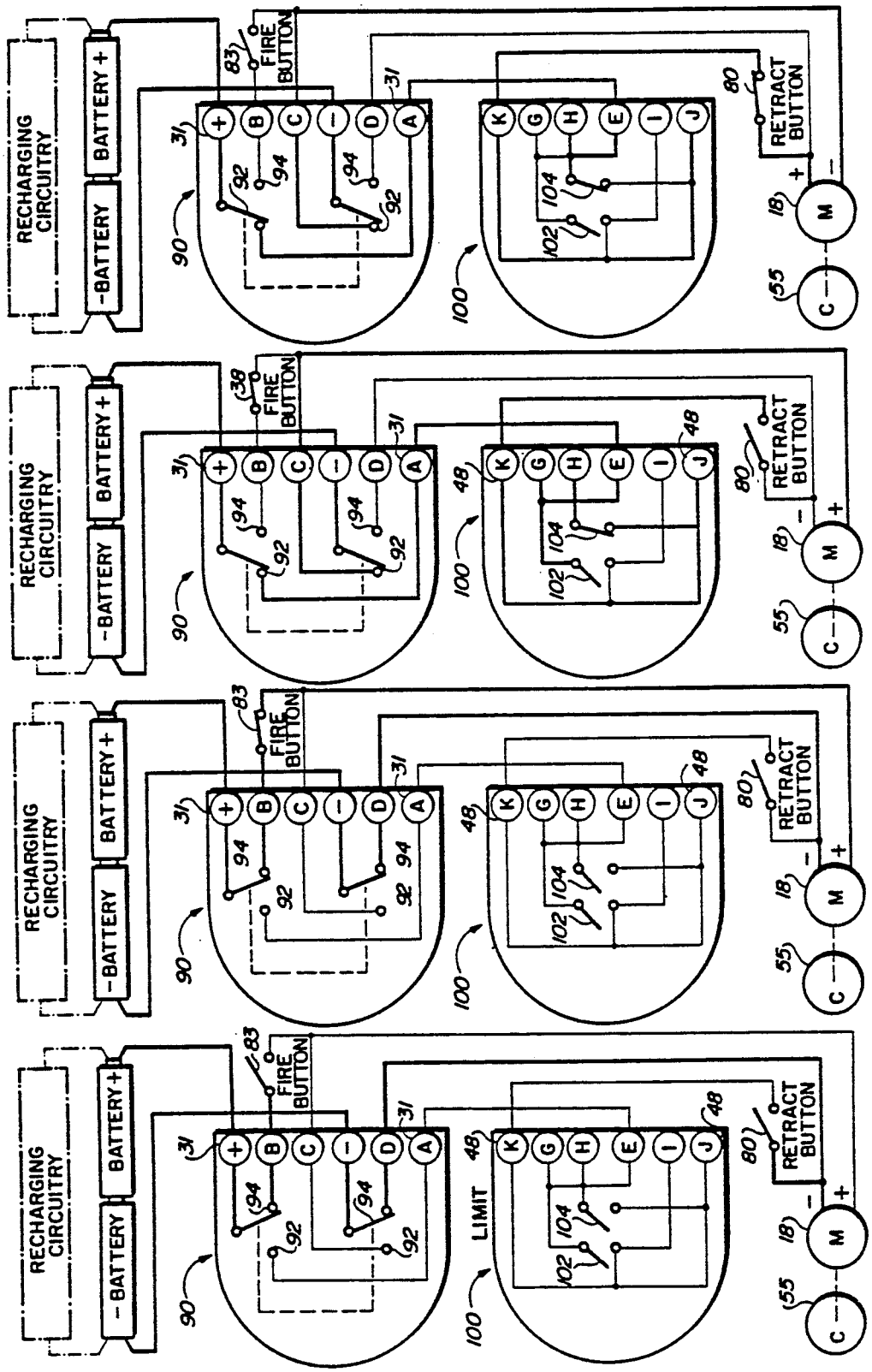

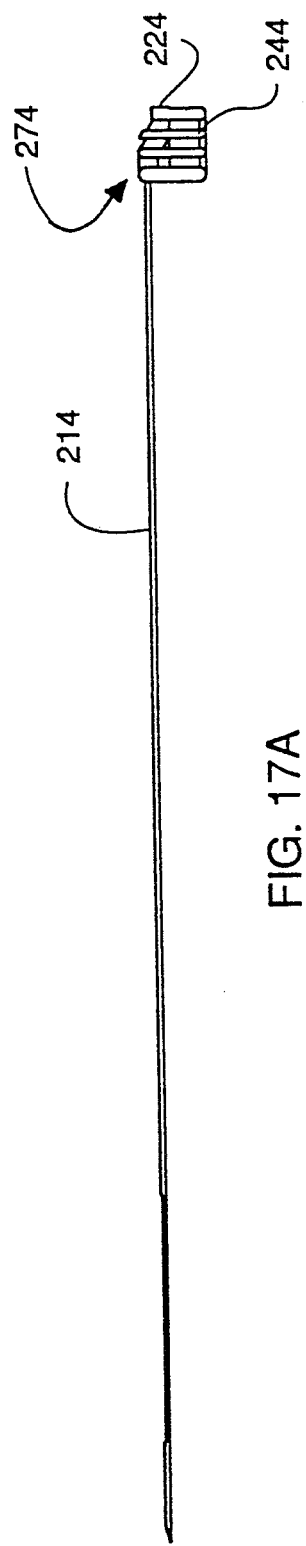
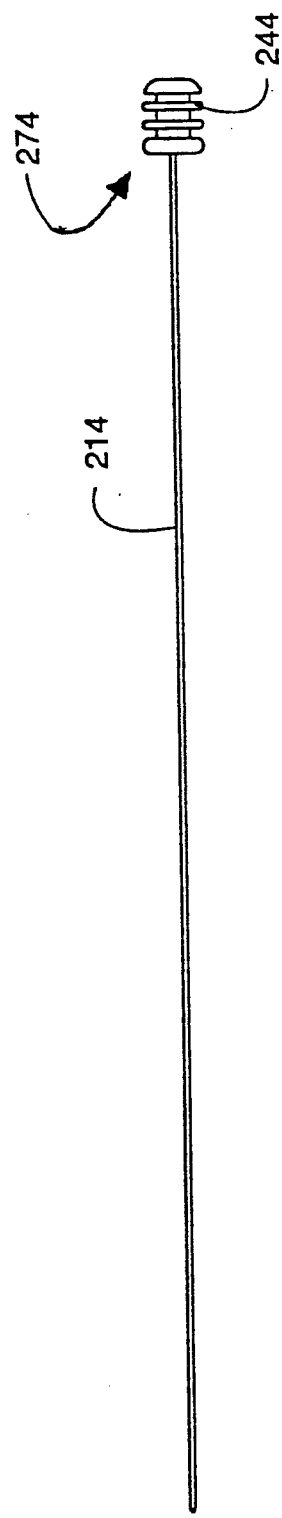
FIG. 17A
FIG. 17B

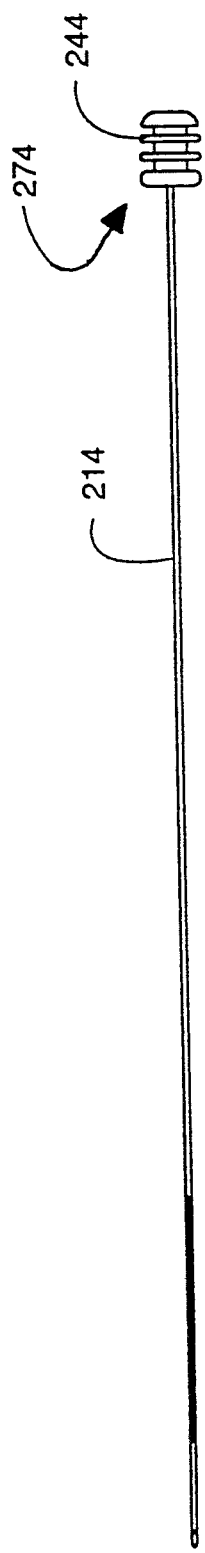
FIG. 17C
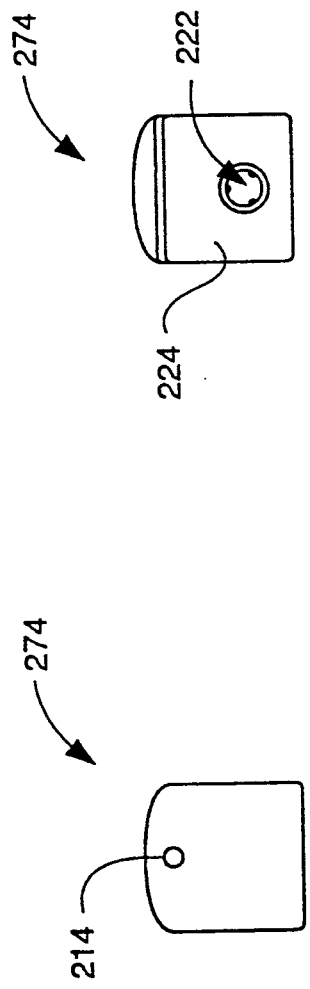
FIG. 17E
FIG. 17D

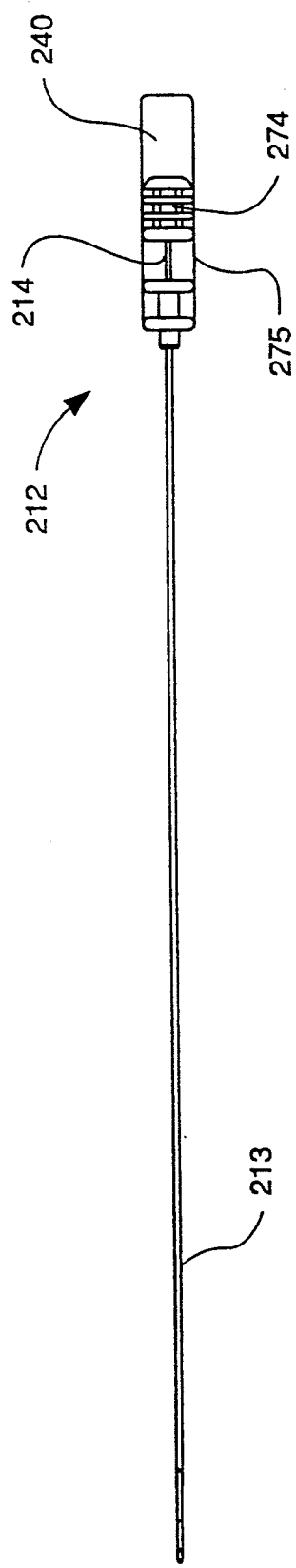
FIG. 18C
FIG. 18E
FIG. 18D

BIOPSY INSTRUMENT STYLET AND CANNULA ASSEMBLY

REFERENCE TO RELATED APPLICATIONS

This application is a continuation-in-part of U.S. patent application Ser. No. 521,259, filed on May 9, 1990, now U.S. Pat. No. 5,048,538, which is a continuation of U.S. patent application Ser. No. 441,776, filed on Nov. 27, 1989 and now issued on Jul. 10, 1990 as U.S. Pat. No. 4,940,061, both by the same inventive entity, and entitled BIOPSY INSTRUMENT.

FIELD OF THE INVENTION

This invention relates to an instrument for extracting samples of tissue from humans and other animals and more particularly to an instrument for automatically performing a biopsy of a tissue mass in an accurate, expeditious manner with a minimum of discomfort to the patient.

BACKGROUND OF THE INVENTION

It is often desirable and frequently absolutely necessary to sample or test a portion of tissue from humans and even other animals, particularly in the diagnosis and treatment of patients with cancerous tumors, pre-malignant conditions and other diseases or disorders. Typically in the case of cancer, when the physical establishes by means of procedures such as palpitation, x-ray or ultra sound imaging that suspicious circumstances exist, a very important process is to establish whether the cells are cancerous by doing a biopsy. Biopsy may be done by an open or closed technique. Open biopsy removes the entire mass (excision biopsy) or a part of the mass (incision biopsy). Closed biopsy on the other hand is usually done with a needle-like instrument and may be either an aspiration or a core biopsy. In needle aspiration biopsy, individual cells or clusters of cells are obtained for cytologic examination and may be prepared such as in a Papanicalaou smear. In core biopsy, as the term suggests, a core or fragment of tissue is obtained for histologic examination which may be done via a frozen section or paraffin section.

The type of biopsy depends in large part in circumstances present with respect to the patient and no single procedure is ideal for all cases. However, core biopsy is extremely useful in a number of conditions and is being used more frequently by the medical profession.

A variety of biopsy needles and devices have been described and used for obtaining specimens of tissue. For example, reference is made to U.S. Pat. Nos. 4,651,752; 4,702,260; and 4,243,048 which shows biopsy needles of varying types. Additionally, a number of very specialized devices for extracting samples of tissue have been described such as the biopsy device in U.S. Pat. No. 4,461,305, which devices is designed specifically for removing a sample of tissue from the female uterine cervix. Other devices have been disclosed which relate to surgical cutting instruments. For example, U.S. Pat. No. 4,589,414 discloses an instrument which is particularly designed to operate in the area of the knee to withdraw tissue chips. Also available are so-called biopsy guns for removing a core of tissue which customarily are spring powered devices and must be cocked with considerable force. When actuated such guns produce a loud snapping noise, combined with a jerking action. Such a biopsy gun may employ a needle set consisting of an inner stylet and an outer tube called a cannula. The stylet is a needle like device with a notched cut-out at its distal end. The cannula in effect is a hollow needle with an angled cutting surface at its distal end which slides over the stylet. When the stylet is forced into tissue, the tissue is pierced and relaxes into the notched cut-out of the stylet. When the cannula is the slid forward, the tissue in the notch of the stylet is sliced off and retained in the notch until the cannula is withdrawn. Examples of such devices are shown in U.S. Pat. Nos. 4,600,014 and 4,699,154. Although such spring powered biopsy guns will remove a core or sample of tissue, they have rather serious disadvantages. For one, they must be manually cocked with a plunger bar. Such "cocking" of the gun requires considerable force and the gun must be cocked for each biopsy cut. A further disadvantage is that the springs provided in the gun accelerate the needles until a mechanical stop position is reached, creating a loud snapping noise and jerking motion which is a problem both to the physician and the patient. This noise and jerking action can cause the patient to jump and in some cases even prevents the physician from striking the intended tissue target. Another disadvantage is that the force and velocity delivered to the stylet and cannula rapidly diminishes when traveling from a retracted to a fully extended position resulting in tissue samples of lower quality.

According it is a principal object of this invention to provide an instrument for obtaining samples of tissue from tissue masses.

It is a further object of this invention to provide a biopsy instrument which is able to provide a substantially constant force and velocity to that portion of the instrument which penetrates the tissue mass and severs a portion of tissue for further examination.

It is another object of this invention to provide an instrument for automatically performing a biopsy of a tissue mass in an accurate and expeditious manner with a maximum of accuracy and a minimum amount of discomfort to the patient.

It is a still further object of this invention to provide an instrument for performing tissue mass biopsies by removing a core or sample of tissue, which instrument eliminates the need for springs and mechanical stops, which is silent in operation and has the ability to effectively penetrate even small tissue masses.

It is another object of this invention to provide an instrument for obtaining tissue samples from tissue masses which instrument requires no manual setting or cocking and which may be "fired" multiple times without any abrupt starts or stops.

It is still another object of this invention to provide a biopsy instrument which includes means to convert rotary motion to sequential, linear motion of substantially constant force and velocity to the means for penetrating and severing a tissue sample from a tissue mass.

These and other objects of the invention will be apparent from the following description and claims.

SUMMARY OF THE INVENTION

Based on the prior art instruments for biopsy samples from tissue masses, and the actual present state of this art, there then exists a need for an instrument which is capable of automatically removing a tissue sample or core sample of pre-determined size where the process is done very rapidly, is easily repeated if required, is accurate, is relatively simple for the physician to use, is virtually noiseless, and in use results in minimal discomfort to the patient.

Accordingly, we have invented an instrument for removing tissue samples from a tissue mass which instrument automatically penetrates, severs, and removes the tissue portion for examination. The instrument is motor powered, preferably by self-contained rechargeable batteries, and employs electrically actuated stops instead of mechanical stops to control the action of penetration and retraction from the tissue mass. The portion of the instrument which penetrates the tissue mass and severs a portion thereof, the tissue penetrating and severing means, includes an inner stylet which penetrates the tissue mass and a hollow outer tube or cannula which surrounds the stylet and serves to sever a sample of tissue. In a preferred form the tissue penetrating end of the stylet is notched so that when the stylet penetrates the tissue mass, a portion of the tissue relaxes in the notched area. After tissue penetration by the stylet, the cannula, having a cutting surface at its distal end, penetrates the tissue and cuts off the tissue portion residing in the notched area of the stylet. The tissue penetrating and severing means are operably connected to a special motor powered rotary cam assembly by means of cam followers and it is a feature of this invention that the rotary motion of the cam is converted to sequential, linear motion in the tissue penetrating and severing means, the linear motion being of substantially constant force and velocity.

In operation, the physician or technician actuates the instrument by pressing a bottom causing the stylet to move forward in a rapid, precise manner and penetrate the tissue mass followed with penetration of the mass by the cannula, resulting in a portion or core of tissue being severed and retained in the notched portion of the stylet. Further actuation by the physician causes the cannula to retract exposing the tissue sample in the stylet for easy removal. An additional actuation causes retraction of the stylet and a resetting of the cannula/stylet assembly for further use.

In a preferred embodiment, the instrument has two actuators or buttons which cycle the action of the stylet/cannula assembly as described above. Actuation of one button, called a fire button, causes penetration of the stylet and cannula into the tissue mass. An initial actuation of the other button, called a retraction button, causes retraction of the cannula to expose a sample of the tissue. A second actuation of the retract button retracts the stylet and the instrument is ready for further use.

Special electrical circuitry allows the stylet/cannula assembly to move in a forward or reverse direction via the rotary motion of a special function cam assembly with a cam travel of approximately 360 degrees. Motion within a single revolution of the cam is controlled via a limit switch assembly, stopping the motion at predefined stylet/cannula assembly locations of, for example: (1) where both the stylet and cannula are forward; (2) where the stylet is forward but the cannula has been moved back; and (3) where both the stylet and cannula are back. The limit switch assembly includes two principal components, a stationary limit switch wiper plate and a rotary limit switch board. The stationary limit switch wiper is provided with spring finger contacts which are electrically connected to the actuation buttons and other circuit components. The rotary limit switch board is a circuit board which is fixed to a rotatable drive shaft and rotates therewith. An electrically conductive circuit pattern is present on one face and the wiper plate and rotary limit switch board are mounted in line in the instrument and in contact with each other concentrically about the drive shaft. As the drive shaft rotates either clockwise or counterclockwise, the circuit pattern on the rotary limit switch board creates particular circuit paths by contacting specific spring finger contacts on the stationary limit switch plate during the rotational motion. The purpose of these specific circuit paths on the rotary limit switch board allows the stylet/cannula assembly to stop at prescribed positions.

The instrument is also provided with what is called a toggle assembly which includes a stationary wiper plate, a toggle board and a toggle plate. The stationary wiper plate is similar to the stationary limit switch wiper plate in the limit switch assembly and is provided with spring finger contacts which are electrically connected to the actuation buttons and other circuit components. The toggle board has an electrically conductive circuit pattern present on one face. The wiper plate and toggle board are mounted in line and in contact with each other concentrically about the drive shaft. As the drive shaft rotates either clockwise or counterclockwise, a key on the drive shaft encounters a protrusion in the central opening of the toggle board. When the key and the protrusion meet the toggle board is forced to rotate a slight distance in a clockwise or counterclockwise direction and the circuit pattern on the toggle board creates again a specific electrical circuit by contacting specific spring finger contacts on the stationary wiper plate. The purpose of the specific circuit paths of the toggle board is to allow the stylet/cannula assembly to travel is prescribed directions either forward or backward via depression of the retract button. This particular construction and circuitry allows the retract button to serve as a dual function switch in the retraction phase of the action of the biopsy instrument. Thus after the forward motion of the stylet/cannula assembly is completed, the retract button can be depressed and the stylet of the stylet/cannula assembly moves backward through approximately one-half a revolution of the special function cam. The limit switch assembly stops the motion at approximately the mid-point of reverse travel of the cam and the toggle board is again mechanically rotated either clockwise or counterclockwise as previously described. The shift in the position of the toggle board changes the electrical circuitry to allow a second actuation of the retract button which permits the continuation of the reverse motion until the limit switch assembly stops rotation of the cam and the cannula is fully retracted.

The present invention further provides a biopsy stylet and cannula assembly suitable for use with a biopsy instrument having a first drive rod and a second drive rod, comprising a cannula mount with a cannula secured thereto and having a recess on the backside of the cannula mount to receive the first drive rod of the biopsy instrument; and, a stylet mount having a stylet secured thereto, wherein the stylet mount also has a recess in a backside thereof for receiving the second drive rod of the biopsy instrument. A locking mechanism may be provided to secure the stylet mount and/or the cannula mount to the drive rods. The stylet and cannula assembly preferably has a generally rectangular frontal profile.

The present invention also provides a biopsy instrument, stylet and cannula assembly including a biopsy instrument with two drive rods, a cannula mount with a cannula disposed on one drive rod, a stylet mount having a stylet secured thereto disposed on the other drive rod, and a mechanism for urging the cannula mount and stylet mount forwardly off of the drive rods for removal. The urging mechanism may comprise a pivoting lever.

The user of the recesses and of the locking mechanisms for securing to the drive rods conceivably could be utilized in biopsy instruments having more conventional spring loaded or other such compression drive mechanisms to power the drive rods.

BRIEF DESCRIPTION OF THE DRAWINGS

The above noted advantages and other characteristics features of the present invention will be in part apparent from the accompanying drawings, and in part pointed out in the following detailed description of the preferred embodiment of the invention in which reference will be made to the accompanying drawings wherein like reference numerals designate corresponding parts and wherein:

FIG. 2 is a side elevational view taken on the line 2—2 of FIG. 1;

FIG. 3 is a part side elevational view taken on the line 3—3 of FIG. 2;

FIG. 3A is a side elevational view taken on the line 3A—3A of FIG. 3;

FIG. 6 is an exploded perspective view of the biopsy instrument illustrating the major component parts thereof;

FIG. 6A and 6B are sectional views of the instrument taken on the lines 6A—6A and 6B—6B respectively of FIG. 6;

FIG. 7 is a plan view of the rotary cam showing the cam grooves;

FIG. 10A-10G are schematic drawings showing the electrical circuitry involved in the various actions of the biopsy instrument;

FIGS. 17A, 17B, 17C, 17D and 17E are a side view, a bottom view, a top view, a front view, and a rear view of a stylet mount and stylet according to the present invention; and, the right side view and left side view are mirror images of one another;

FIGS. 18A, 18B, 18C, 18D and 18E are a side view, a bottom view, a top view, a front view, and a rear view of a stylet and cannula assembly according to the present invention; and, the right side view and left side view are mirror images of one another;

DESCRIPTION OF THE PREFERRED EMBODIMENT

Figure 1:
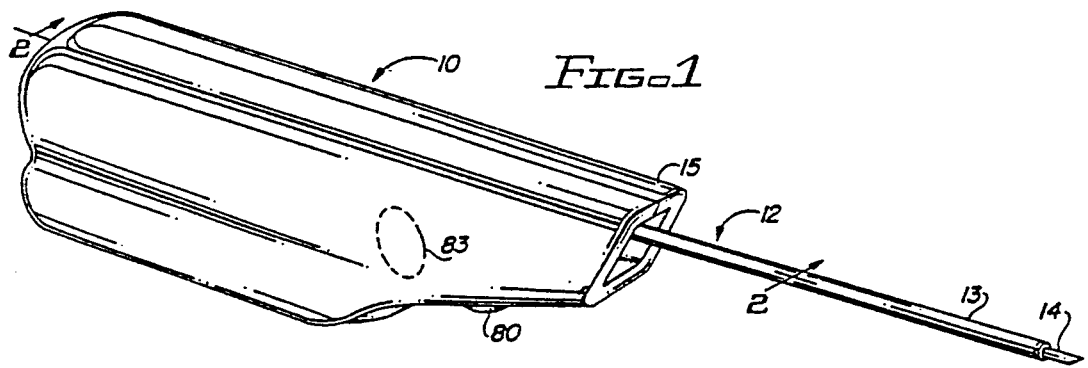
FIG. 1 is a perspective view of the biopsy instrument of this invention.
Figure 5:
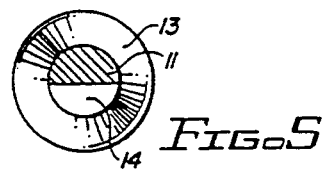
FIG. 5 is a cross section of the stylet/cannula assembly taken on the line 5—5 of FIG. 4D.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Considering now the drawings in detail, FIG. 1 illustrates a perspective view of one embodiment of the inventive biopsy instrument which is shown generally at 10 with the tissue piercing and removing means shown generally at 12. The tissue piercing and removing means comprises a stylet 14 and cannula 13. Referring to FIG. 2 which is a sectional view through the instrument shown in FIG. 1, and FIG. 6, which is an exploded view of a number of the components of the instrument, the instrument 10 is shown as having an outer housing 15 provided with a motor 18 mounted in one end thereof. Motor 18 is reversible and preferably of the DC type and preferably powered by rechargeable batteries 16 contained within the housing. Suitable contacts 17 are provided to recharge the batteries. Motor 18 is operably engaged with planetary gear assembly 20 by means of shaft 19 which shaft engages central gear 21. Central gear 21 in turn meshes with planetary gears 22 which in turn engage with annulus gear 23. In a preferred embodiment the DC motor operates at about 10,000 rpm with the gearing being about a 6:1 ratio. One end of the planetary gear set 20 is mounted in bearing 24 which in turn is secured within the housing the bracket 39. Drive shaft 25 is secured at its end 26 in the D-shaped opening 35 of the planetary gear set by means of a set screw or other suitable fastening means.

Figure 8:
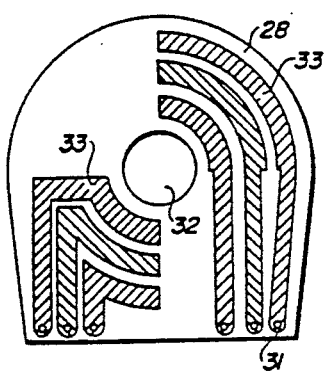
FIG. 8 is an elevational view of one side of the wiper assembly.
Figure 9A:
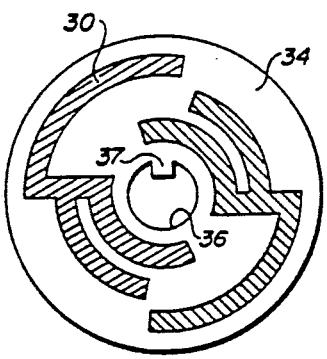
FIG. 9A is an elevational view of one side of the toggle printed circuit board.

Positioned adjacent to the gear assembly are the means for controlling the movement of the stylet/cannula assembly 12 in a forward (piercing) direction or in a reverse direction with respect to the tissue mass. Such means includes a toggle assembly comprising stationary wiper plate 28, a toggle board 34 and a toggle plate 40. Positioned adjacent to the toggle assembly is a limit switch assembly comprising a limit switch wiper plate 45 and a limit switch board 50, all as best shown in FIG. 6. Stationary wiper plate 28 is provided with a central opening 32 for passage of drive shaft 25. On one side of wiper plate 28 is a series of vertically positioned contact pins 29. Along the base of the wiper plate are a series of wire contact posts 31. As shown there are six spring contact pins and six contact posts. As shown in FIG. 8, the reverse side of stationary wiper plate 28 is provided with a series of electrically conductive circuit paths 33 with one end of each circuit path connected to a wire contact post 31 and the other end connected to a contact pin 29. Immediately adjacent to the stationary wiper plate 28 is circular shaped toggle board 34 having a central opening 36 for passage of drive shaft 25 with a protrusion 37. Positioned toward the outer edge of toggle circuit board 34 and on one side thereof is pin 38. As shown in FIG. 9A, the reverse side of the toggle circuit board 34 is provided with a series of electrically conductive circuit paths 30. Certain of the spring contact pins 29 make contact with circuit paths 30.

The toggle assembly is completed by the toggle path 40 mounted and positioned within the instrument by bracket 41. Again as shown in FIG. 6, the toggle plate is provided with a central rectangular opening 40a, V-shaped opening 43 and spring 42 which is secured to an inner wall of housing 15. In the assembled instrument, pin 38 of toggle board 34 rides within V-shaped opening 43 and this combination serves to control the amount of rotary movement of the toggle board. The toggle board can rotate a distance in either a clockwise or counterclockwise direction and the amount of rotation is controlled by pin 38 in V-groove 43.

Figure 9B:
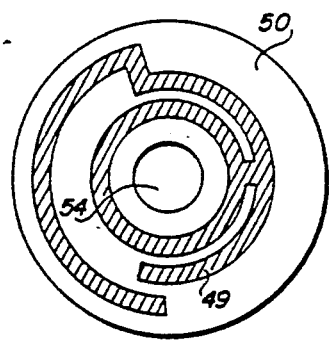
FIG. 9B is an elevational view of one side of the wiper assembly of the limit switch assembly.

Adjacent to the toggle assembly is the limit switch assembly made up of stationary limit switch wiper plate 45 and limit switch board 50. Wiper plate 45 is similar in construction to the stationary wiper plate 28 of the toggle assembly having a central opening 46 and being provided on one side thereof with a series of vertically positioned contact pins 47 and a series of wire contact posts 48 along the base of the wiper plate 45. The contact pins 47 make direct contact with a side of the limit switch board 50 and this side of the limit switch board is shown in FIG. 9B. As with the stationary wiper plate 28 and the toggle board 34, board 50 has a central opening 54 and electrically conductive circuit paths 49. Limit switch board 50 rotates with drive shaft 25 and is therefore provided with a split collar 51 for passage of the shaft 25. Clamp 52 surrounds the collar 51 and when tightened by screw 53 insures that the limit switch board will rotate with shaft 25.

The components of the instrument which guide the stylet/cannula assembly 12 will now be detailed. As previously described, the physician or technician actuates the instrument causing the stylet 14 to move forward in a rapid and precise manner to penetrate the tissue mass followed by penetration of the mass by the cannula 13, resulting in a portion or core of tissue being severed and retained in the notched portion of the stylet. Further actuation causes the cannula to retract exposing the tissue sample in the notched portion at the distal end of the stylet for easy removal. An additional actuation causes retraction of the stylet and a resetting of the cannula/stylet assembly for further use. The penetration and retraction of the stylet and cannula assembly is controlled in part by hollow rotary cam 55 which is best illustrated in FIGS. 6 and 7. Cam 55 is provided with a continuous groove 56 and a preferred groove pattern is shown in even greater detail in FIG. 7. As shown, continuous groove 56 is made up of three sections. A first groove section 56a is positioned substantially parallel to one end of cam 55 and extends about a portion of the circumference of the cam. A second groove section 56b is positioned substantially parallel to the other end of the cam and also extends about a portion of the circumference of the cam. Section 56c connects section 56a and 56b in a generally diagonal manner. Cam 55 is rotated by means of drive shaft 25 and, as partly shown in FIGS. 4A–4D, this is accomplished by securing shaft end 26 into the opening 63 of the end wall 59 of cam 55. Thus rotation of shaft 25 in a clockwise or counterclockwise direction causes identical rotation of the cam. Housing 58 surrounds cam 55 and serves to properly position the cam within the instrument.

As previously described stylet 14 moves within and is surrounded by cannula 13. The non-penetrating end of stylet 14 is mounted in stylet block 74. Correspondingly, the non-penetrating end of cannula 13 is mounted into cannula block 75. As shown in FIG. 6, stylet block 74 is provided with extension 76 which is in alignment with and moves through opening 77 of the cannula block 75 to aid in proper alignment of the stylet and cannula blocks and therefore the stylet/cannula assembly.

Mounted in the ends of each of the cannula and stylet blocks are drive rods 62 which rods are in turn secured to drive arms 61. Each of drive arms 61 is provided with cam follower 60, which ride in the continuous groove 56 of cam 55. Thus, rotation of cam 55 will result in sequential linear movement of the stylet and cannula.

Figure 4A:
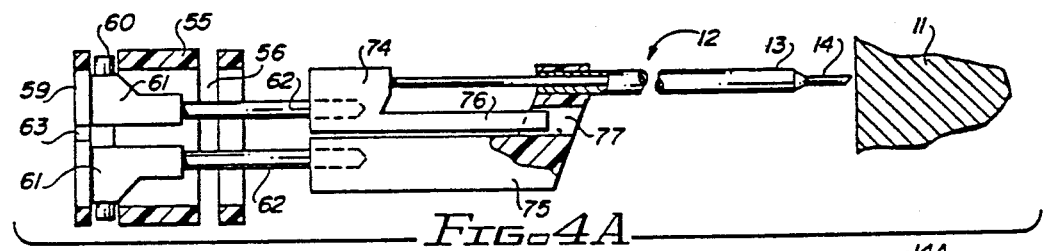
FIG. 4A-4D are part side elevational views showing the action involved in penetration of a tissue mass by the stylet and cannula and retraction of the cannula from the tissue mass.
Figure 4B:
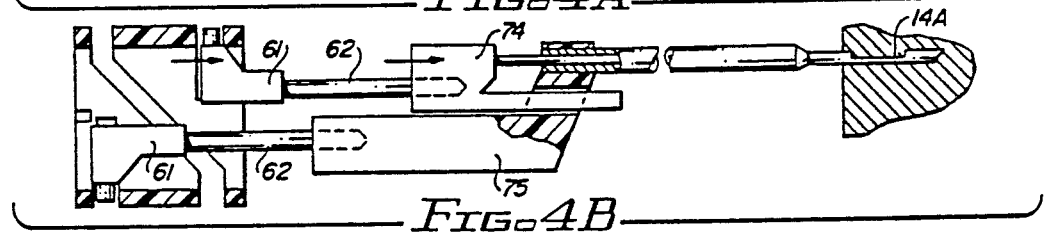
Figure 4C:
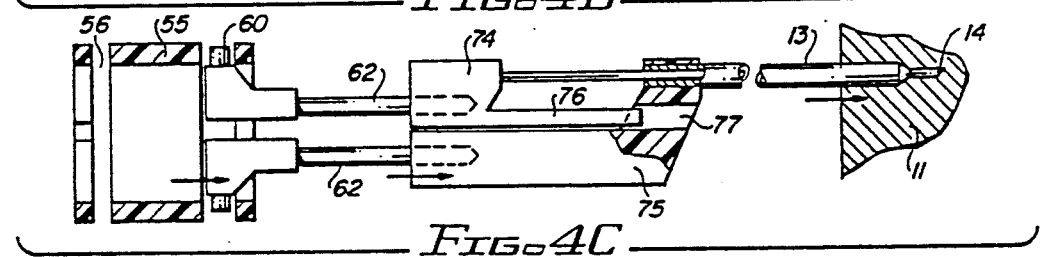
Figure 4D:
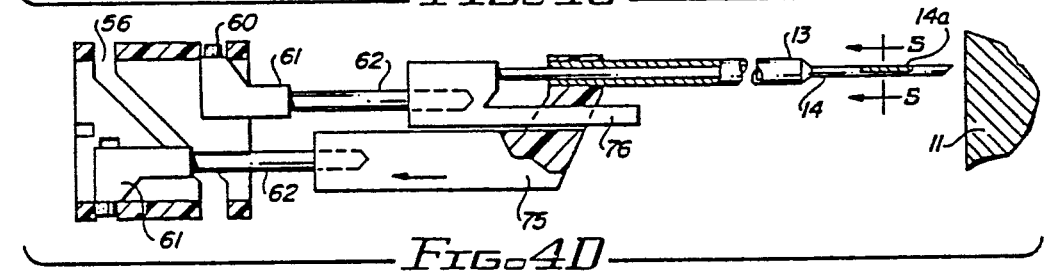

This sequential linear movement is well illustrated in FIGS. 4A–4D. In FIG. 4A, each of the stylet 14 and cannula 13 are in a retracted position and immediately adjacent the tissue mass 11. Initial rotation of cam 55, as shown in FIG. 4B, results in lateral movement of stylet block 74 and its attached stylet to penetrate the tissue mass where a portion of the tissue is caught in notch 14a. Continued rotation of the cam, as shown in FIG. 4C, results in the movement of the cannula block 75 and its attached cannula into the tissue mass severing the portion of the tissue within notch 14 from the tissue mass. As shown in FIG. 4D, rotation of cam 55 has been reversed thus causing retraction of the cannula exposing the tissue sample in notch 14a for easy removal by the technician. Further rotation of cam 55 will result in retraction of the stylet and the instrument is again ready for use as shown in FIG. 4A.

Because of the need for precise movement of stylet and cannula, guide means shown generally at 64 are used to further aid in proper alignment of the stylet/cannula assembly. As shown in FIGS. 6, 6A and 6B, guide means 64 includes a generally cylindrical shaped housing 68 having a rectangular opening 69 approximately sized to accommodate the stylet and cannula blocks 74 and 75. Thus the stylet and cannula blocks move laterally within the interior of housing 68 and bear on the interior walls of the housing aiding proper alignment. In addition, guide means 64 also includes a cylindrical shaped guide 65 and bulkhead 70, the latter separating guide 64 and housing 68. Guide 65, as best shown in FIG. 6B, is a solid cylinder provided with vertical channels 66 through which drive rods 62 operate. Guide 65 is so constructed that separator 71 is provided between channels 66 to assist in maintaining proper spacing and alignment of the drive rods.

In a preferred embodiment, the instrument has two actuators or buttons which set as to motion the action of the stylet/cannula assembly. Actuation of the fire button, causes initial penetration of the stylet into the tissue mass followed by penetration of the cannula. The initial actuation of the retract button, causes retraction of the cannula exposing the sample of tissue. A second actuation of the retract button retracts the stylet and the instrument is ready for further use.

Thus, as shown in FIGS. 2 and 3, the instrument includes retract button 80 and a fire button 83, both of which are preferably provided with a rubber seal. As shown in FIG. 2, the retract button is located on the underside of the instrument. Depression of the retract button engages contacts 81 completing the circuit and allowing current to flow into wire 82. As illustrated in FIG. 3, fire button 83 is located away from the retract button and on one side of the instrument. The depression of fire button 83 actuates micro switch 85 by means of lever 84 mounted on pivot pin 86.

The biopsy instrument is provided with an assembly and circuitry which permits the stylet/cannula assembly to move in a forward or reverse direction via the rotary motion of the special function cam assembly with a rotation of approximately 360 degrees. Rotation of cam 55 is controlled via the limit switch assembly, stopping the rotation at pre-defined stylet/cannula assembly locations of, for example: (1) both the stylet/cannula are forward; (2) the stylet is forward but the cannula has been moved back; and (3) where both the stylet and cannula are back. Such limit switch assembly is composed of two principal components, stationary limit switch wiper plate 45 and rotatable limit switch board 50. Stationary wiper plate 45 is provided with six spring finger contacts 47 which are electrically connected to the actuation buttons 80 and 83 and other circuit components. The limit switch board 50 is a circuit board which is fixed to the drive shaft 25. An electrically conductive circuit pattern is present on one face thereof and the wiper plate 45 and rotatable limit switch board are mounted in line in the instrument and in contact with each other concentrically about the drive shaft. As the drive shaft rotates clockwise or counterclockwise, the circuit pattern on the rotatable limit switch board creates particular circuit paths by connecting specific spring finger contacts during the rotational action. The purpose of these specific circuit paths on the rotatable limit switch board allows the stylet/cannula assembly to stop at prescribed positions.

The instrument is also provided with a toggle assembly which includes a stationary wiper plate 28, toggle board 34 and toggle plate 40. The stationary wiper plate is very similar to the stationary limit switch wiper plate 45 in the limit switch assembly and is also provided with six spring finger contacts 29 which are an electrical contact with the actuation buttons and other circuit components. Toggle board 34 has electrically conductive circuit pattern 30 deposited on one face. Wiper plate 28 and toggle board 34 are mounted in line and in contact with each other concentrically about the drive shaft 25. As the drive shaft rotates either clockwise or counterclockwise, key 27 on shaft 25 contacts protrusion 37 on the toggle board. When the key and protrusion meet the toggle board is forced to rotate a slight distance in clockwise or counterclockwise direction and the circuit pattern on the toggle board creates a particular circuit path by being in contact with specific spring fingers 29. The amount of rotation of the toggle board is controlled by pin 38 riding in V-shaped opening 43. The purpose of the specific circuit paths of the toggle board is to allow the stylet/cannula assembly to travel in prescribed directions of motion via depression of the retract button 80. This particular construction allows the retract button 80 to serve as a dual function switch in the retraction phase of the biopsy instrument. After the forward motion of the stylet/cannula assembly is completed, retract button 80 can be pressed and the stylet of the stylet/cannula assembly moves back or retracts resulting from approximately one-half a revolution of the special function cam. The limit switch assembly stops the rotation at approximately the mid-point of reverse travel and the toggle board is mechanically rotated as previously described. The shift in the position of the toggle board 34 changes the electrical circuitry to allow a second actuation of the retract button which continues the cam rotation until the limit switch assembly stops rotation at the end of travel and the cannula is fully retracted.

FIGS. 10A-10G illustrate schematically the basic circuitry involved in various actions of the biopsy instrument. In these figures, the circuitry and activity of the toggle assembly is shown generally at 90, and the circuitry and activity of the limit switch assembly is shown generally at 100. Connectors 31 of the stationary wiper plate 28 of the toggle assembly are designated "+", "B", "C", "−", "D" and "A". Connectors 48 of the limit switch wiper plate 45 are designated "K", "G", "H", "E", "I", and "J". In the limit switch assembly schematic 100, the arm limit switch is designated 102 and the sample limit switch is designated 104. In the toggle assembly schematic 90, the positions of the rotatable toggle board 34 are designated either 92 or 94. Closing the arm limit switch 102 initiates the sequential, linear forward motion of both the stylet and cannula. The arm limit switch 102 thus controls the sequential forward movement of the stylet/cannula assembly. The sample limit switch 104 controls the retraction of the cannula. The path of the current flow of all figures 10A-10G is shown with bold lines.

FIG. 10A illustrates a ready to fire situation; that is, both the stylet and cannula are fully retracted. The toggle board 34 has rotated with an imaginary point on the shaft 25 or cam 55 being at 0 degrees. As shown in FIG. 10A, the position of the toggle board is at 94 which allows current to flow only to fire button 83. Both the arm limit switch 102 and the sample limit switch 104 are open and the retract button is therefore not in the circuit and even if depressed, no action would occur.

FIG. 10B illustrates what happens when the fire button is depressed. Depression of the fire button sends current to the motor "M" causing rotation of the cam "C" 55 and forward movement of the stylet and cannula. As shown in the limit switch assembly 100 of FIG. 10B, both the arm limit switch 102 and sample limit switch 104 are open and no current is flowing through the limit switch assembly.

FIG. 10C illustrates the situation at the end of the fire cycle shown in FIG. 10B. At this point, shaft 25 and cam 55 have rotated approximately 320 degrees from an initial 0 degree position and each of the stylet and cannula have moved sequentially to a fully extended position. Key 27 on shaft 25 has made contact with protrusion 37 of toggle board 34 to rotate toggle board 34 which in turn causes the toggle switches to move from position 94 to position 92. This movement of the toggle switches results in a break in the circuit path to motor M. In the limit switch assembly 100, the arm limit switch 102 is open, and the sample limit switch 104 is closed. Both the stylet and cannula are forward.

In FIG. 10D, the circuit at fire button 83 is now open and the toggle switches of the rotatable toggle board 34 are at the position designated 92, as they were at the end of the fire cycle shown in FIG. 10C. The toggle board in this position allows current to flow to the retract button 80 via the limit switch assembly circuit. As shown in the limit switch assembly circuit 100, the sample limit switch 104 is closed and the arm limit switch 102 is open. Thus, depression of retract button 80 causes the motor M to reverse, causing rotation of the cam to reverse, resulting in retraction of the cannula.

Figure 10G:
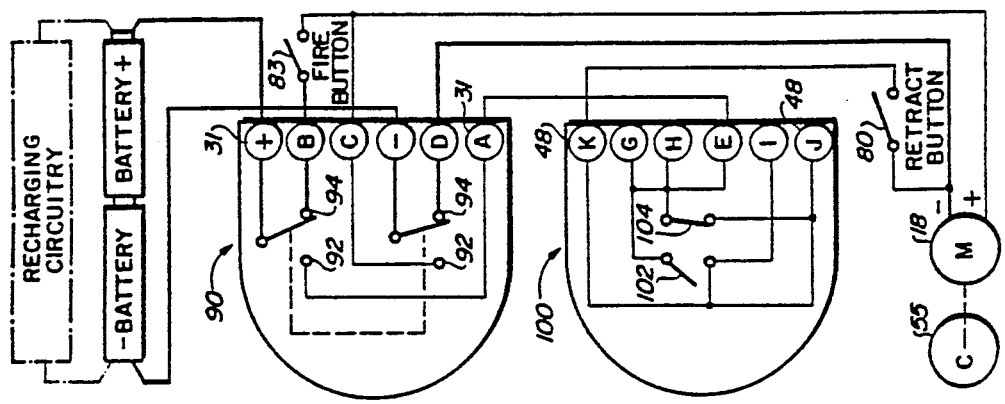
Figure 10F:
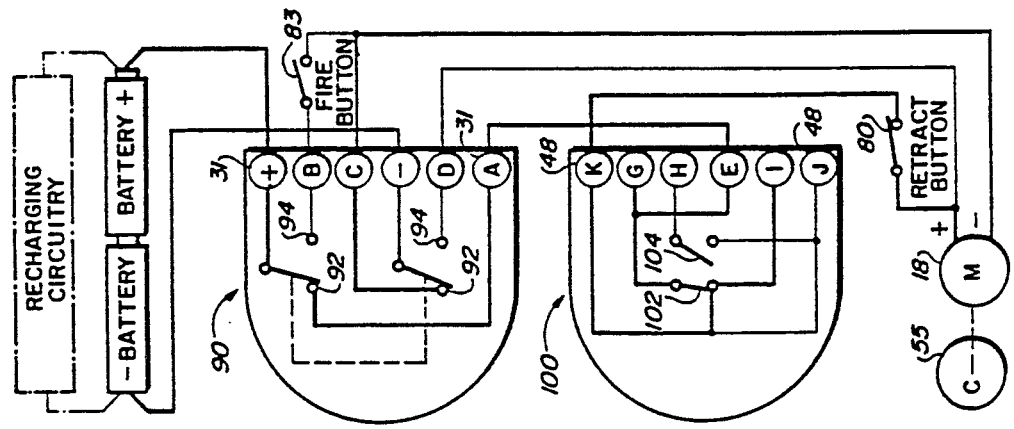
Figure 10E:
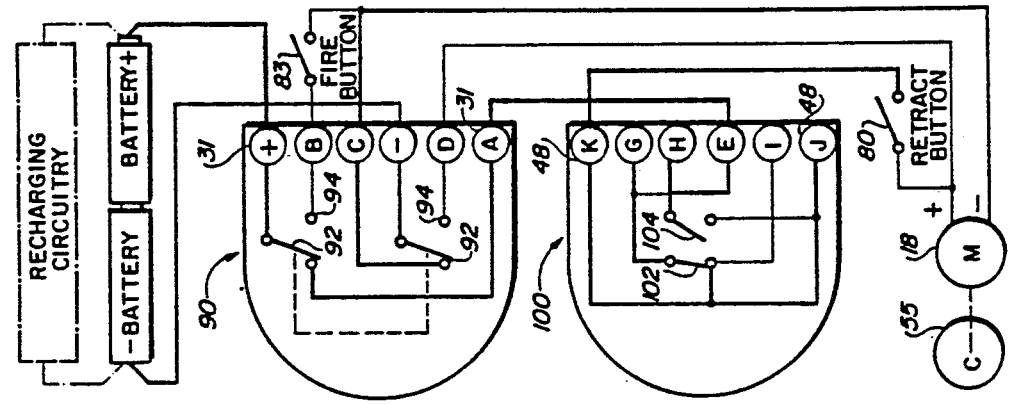

In FIG. 10E, the toggle switches of the toggle board are at position 92 and in this position actuation of the fire button would have no effect. In the limit switch assembly circuit 100, arm limit switch 102 is closed and the sample limit switch is open. The retract button circuit 80 is open preventing any further cam motion. In this situation, the cannula is back and the stylet is forward.

FIG. 10F, shows the activity upon a second depression of the retract button 80. In the toggle assembly 90, the toggle board switches are in the position designated 92 which allows current to flow to the retract button via the limit switch assembly circuit 100. The arm limit switch 102 is closed. When the retract button is depressed motor M operates retracting the stylet and thus both the stylet and cannula are in a ready to fire position.

FIG. 10G illustrates the situation of the end of the retraction of both the stylet and cannula. At the end of the retraction cycle, the drive shaft key moves the toggle board to a 20 degree rotation point. In the limit switch assembly 100, the arm limit switch 102 is open and the sample limit switch 104 is closed. Thus the retract button is not in the circuit at this point, and no action will occur even if depressed.

Figures 14A, 14B:
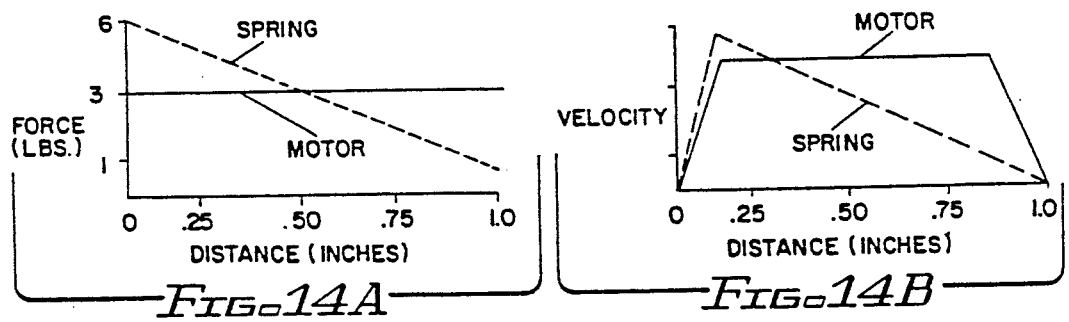
FIGS. 14A and 14B are graphs comparing the force and velocity delivered by the tissue penetrating and severing means of a typical spring powered biopsy gun and the instrument of the present invention.
Figure 11A:
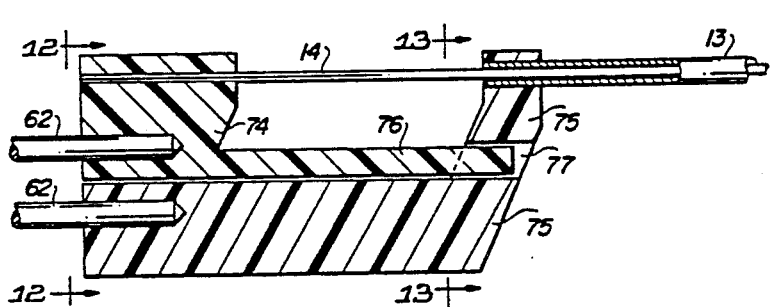
FIG. 11A and 11B are part side sectional views of the biopsy instrument showing the action and construction of the cannula and stylet blocks.
Figure 12:
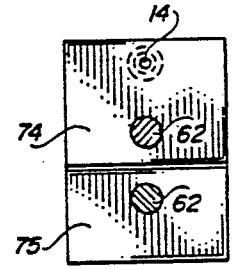
FIG. 12 is a section taken on the line 12—12 of FIG. 11A.
Figure 11B:
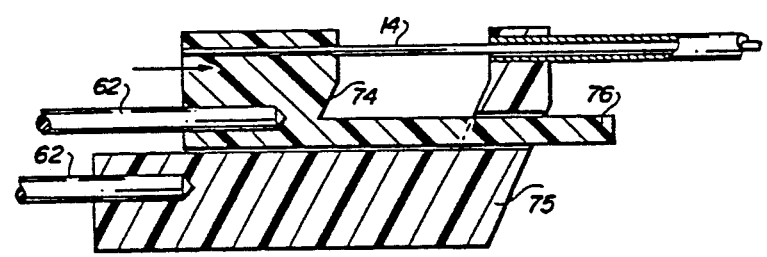
Figure 13:
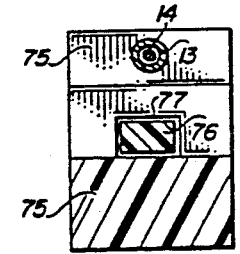
FIG. 13 is a section taken on the line 13—13 of FIG. 11A.

One of the features of the instrument of this invention is its ability to deliver a substantially constant force and velocity to the tissue penetrating and severing means, that is the stylet and cannula, thereby obtaining a higher quality tissue sample. This is graphically illustrated in FIGS. 14A and 14B where the force and velocity of a typical spring powered instrument (indicated by a dashed line) is compared with the biopsy instrument of this invention (indicated by a solid line). Assuming that the stylet and cannula travel a distance of about 1 from a retracted to a fully extended position, as shown in FIG. 14A it will be seen that the instrument of this invention delivers a virtually constant force to the stylet and cannula from a retracted to fully extended position. On the other hand, the spring powered instrument, although initially delivering a considerably greater force, this force diminishes very rapidly due to tissue resistance and spring characteristics. Substantially the same is true with respect to the velocity of the stylet and cannula of the two instruments. As shown in FIG. 14B, although the initial velocity of each instrument is about the same, the instrument of this invention delivers a constant velocity over almost all of the travel of the stylet and cannula whereas in the spring powered instrument the velocity again diminishes very rapidly throughout the required travel.

Referring to FIGS. 15A-15F, a second embodiment of the invention is shown generally is biopsy instrument 210 having a second embodiment of a stylet/cannula assembly shown as 212. The stylet and cannula assembly 212 and its component parts are illustrated in FIGS. 16A-16E, 17A-17E, 18A-18E, 19A and 19B.

Biopsy instrument 210 is substantially the same as biopsy instrument 10 previously described with certain modifications and refinements. One such improvement is the presence of lever 286 at front end 271 of the biopsy instrument. As illustrated in FIGS. 15A-15F, lever 286 has pivot 288 located between handle end 289 and cam end 287. Pivot 288 (shown in phantom lines in FIG. 15A) is pivotably attached to front end 271 alongside of rectangular opening 269 which receives stylet mount 274 and cannula mount 275 therein. As described with instrument 10, biopsy instrument 210 has two drive rods in the front end 271 for successively moving the mounts for cannula 213 and stylet 214. Lever 286 enables the operator to more easily remove stylet mount 274 and cannula mount 275 from opening 269.

Figure 15A:
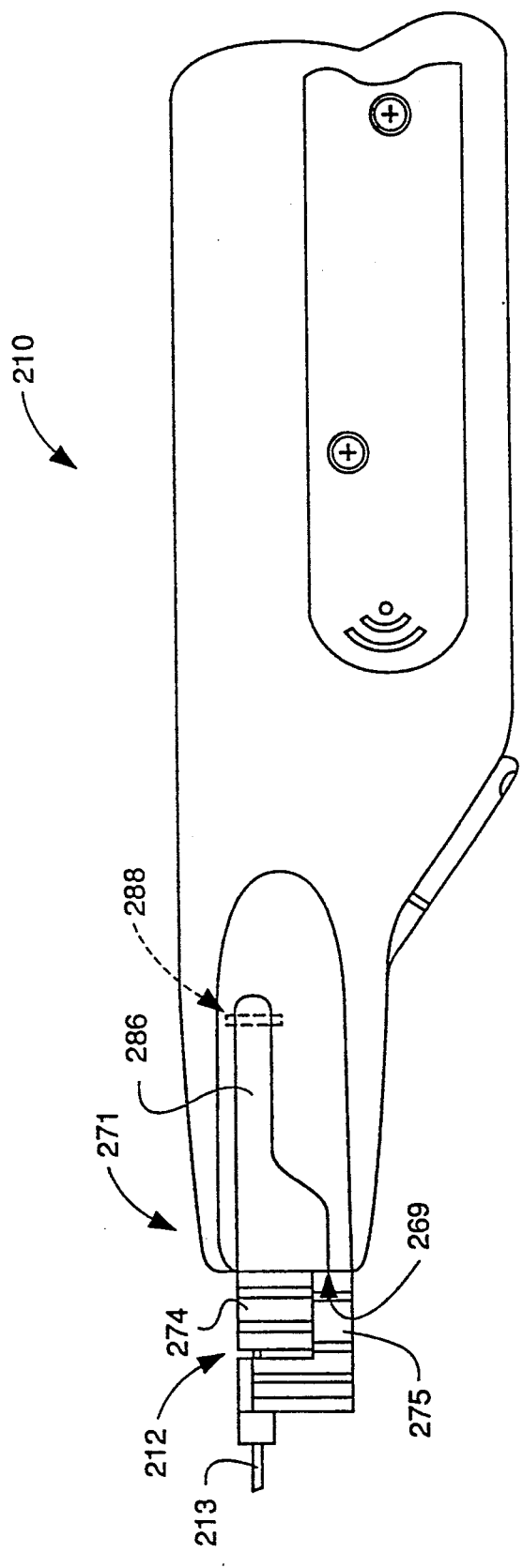
FIG. 15A is a side view of an alternative embodiment of the biopsy instrument of this invention showing a stylet and cannula assembly being inserted in a front end thereof.
Figure 15B:
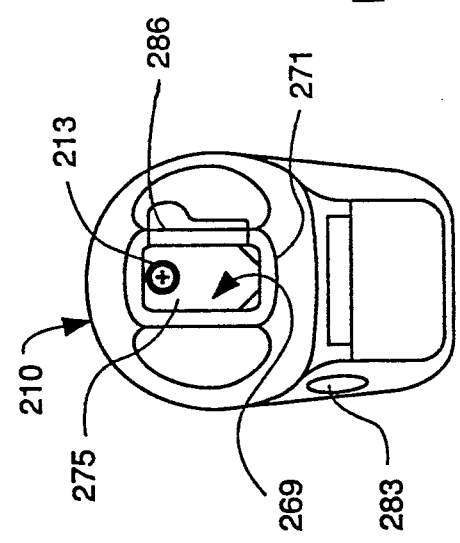
FIG. 15B is a front view of the device of FIG. 15A.
Figure 15C:
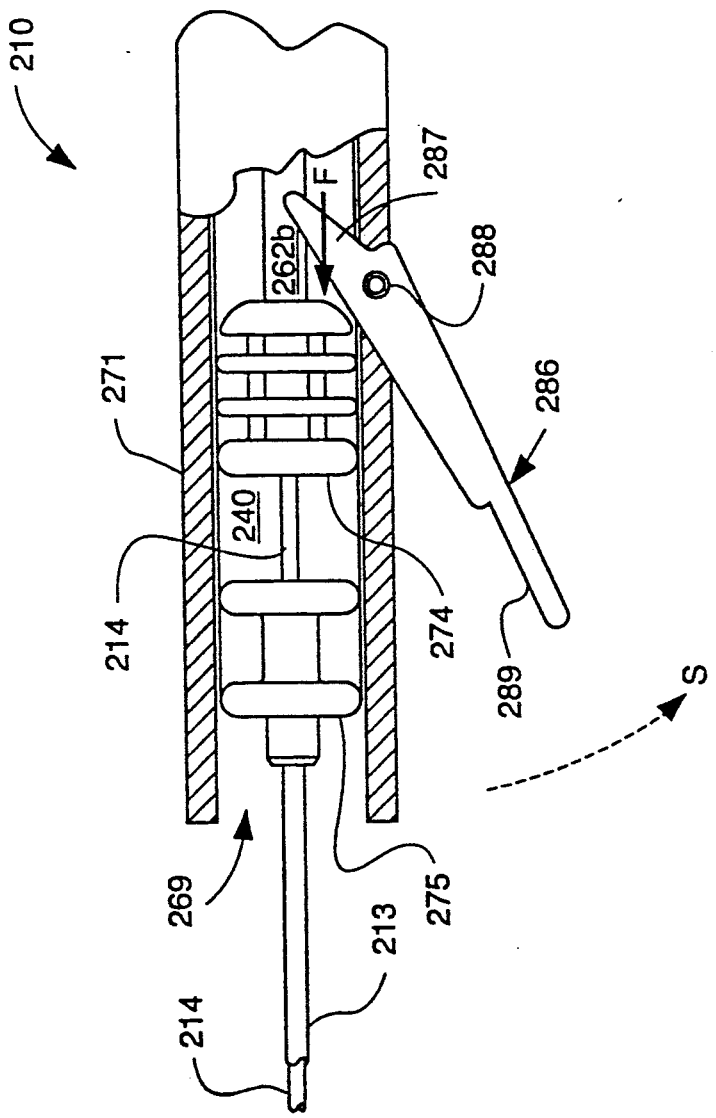
FIG. 15C is a partially cut away top view of the front end of the alternative embodiment of the biopsy instrument showing lever 286 pivoted outwardly.
Figure 15D:
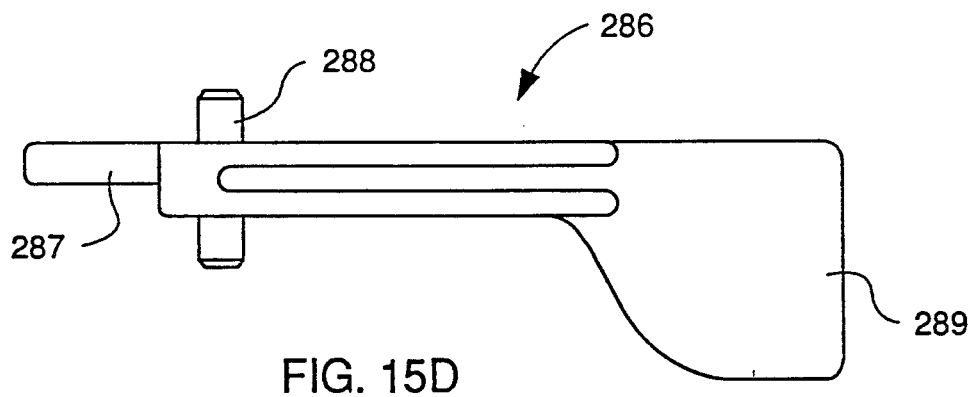
FIG. 15D is an inside side view of the lever used in the device of FIG. 15C.
Figure 15E:
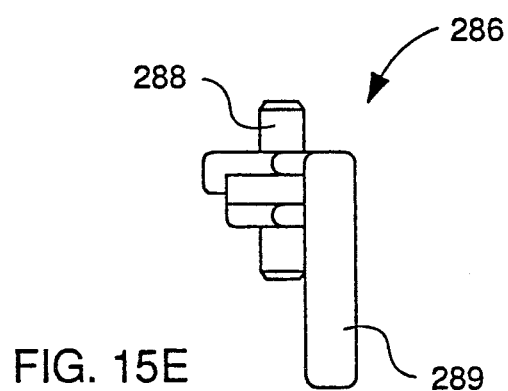
FIG. 15E is a front view of the lever of FIG. 15D.
Figure 15F:
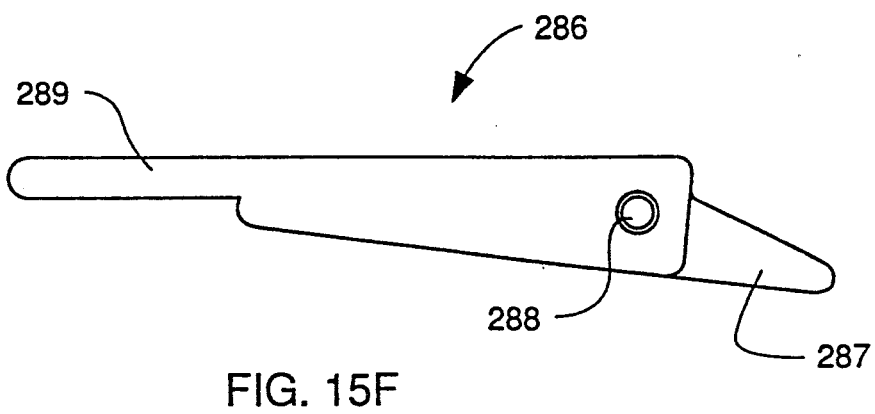
FIG. 15F is a bottom view of the lever of FIG. 15D.

As shown in FIG. 15C, lever 286 may be swung outwardly in the direction of arrow "S" by the operator pulling outwardly on handle end 289. This causes lever 286 to pivot about pivot 288, causing cam end 287 to apply force "F" along the back side of stylet mount 274. Note that optionally mount 274 has a rounded back surface to more smoothly engage with cam end 287. The force against mount 274 correspondingly exerts force on mount 275, urging both of the mounts 274 and 275 forwardly off of drive rod 262a and 262b. Of course, lever 286 may be made to engage mount 275 as well. Furthermore, other mechanisms may be provided to forwardly urge the mounts off the drive rods, such as a wedging mechanism, a threaded screw mechanism, or the like.

Thus, this mechanism for urging the mounting blocks off the drive rods is especially useful in conjunction with another feature of the present invention, described below, which provides a locking mechanism to lock the cannula mount and stylet mount on the drive rods.

Another optional feature (not illustrated) is lever 286 may have a stop member projecting laterally inward from end 289 across opening 269 when lever 286 is in a closed or loaded position. Such stop member acts to block the stylet and cannula mounts from being projected out of opening 269 upon firing of the biopsy device, and yet swings out of the way during removal of the mounts such as illustrated generally in FIG. 15C.

Biopsy instrument 210 includes firing button 283. Also, instrument 210 may optionally have a modified cam, like cam 55, with section 56c of the cam groove modified so its slope is not constant, but instead varies somewhat near sections 56a and 56b. In this way, the velocity of the stylet and cannula are not necessarily constant, but it is believed improved performance can be achieved.

Stylet and cannula assembly 212 include cannula mount 275 having a tubular cannula 213 secured thereto and projecting forwardly therefrom. Cannula mount 275 has drive rod recess 223 in backside 225 of the cannula mount. This recess is sized and positioned for receiving drive rod 262a (see FIG. 19A) of the biopsy instrument therein. Similarly, stylet mount 274 has drive rod recess 22 therein in backside 224 of the stylet mount for receiving drive rod 262b therein. Stylet mount 274 has stylet 214 secured thereto, projecting forwardly and located within tubular cannula 213. Stylet 214 is slidable through cannula 213 as described above with cannula 13 and stylet 14. Stylet mount 274 slides along a top side 240 of a bottom portion 238 of cannula mount 275. Cannula mount 275 also includes a forward portion 239 which projects above top side 240 of bottom portion 238 of the cannula mount. In this way, front portion 239 is in front of stylet mount 274, providing forward confinement for stylet mount 274.

Figure 16A:
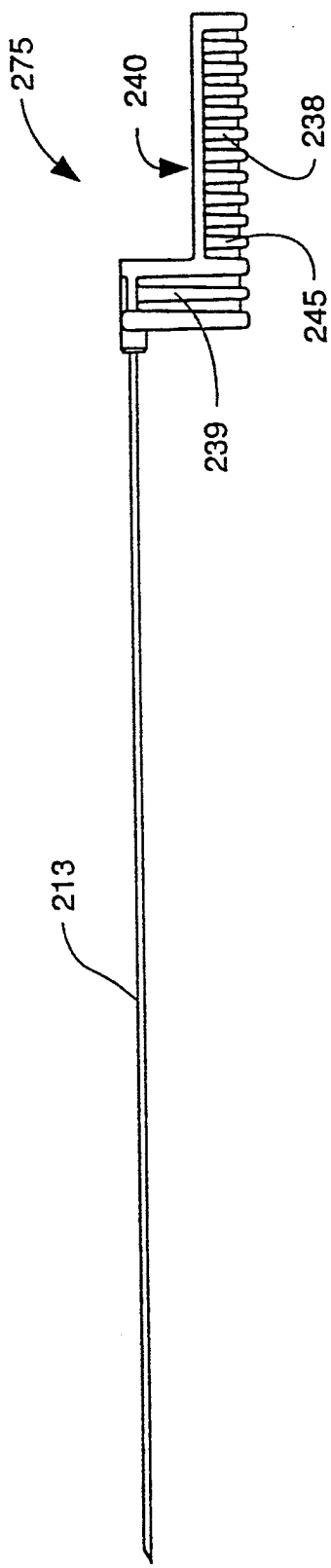
FIGS. 16A, 16B, 16C, 16D and 16E are a side view, a bottom view, a top view, a front view, and a rear view of a cannula mount and cannula according to the present invention; and, the right side view and left side view are mirror images of one another.
Figure 16B:
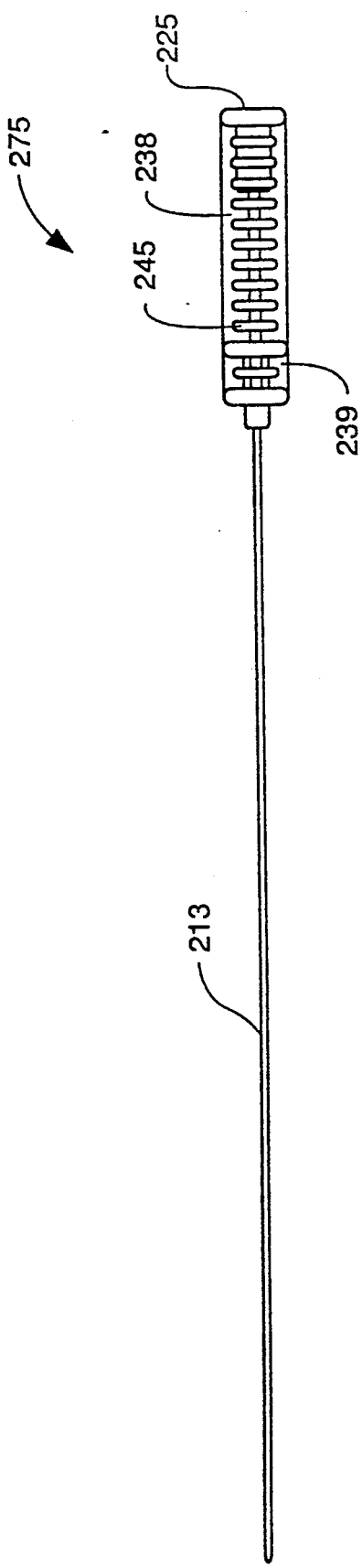
Figure 16C:
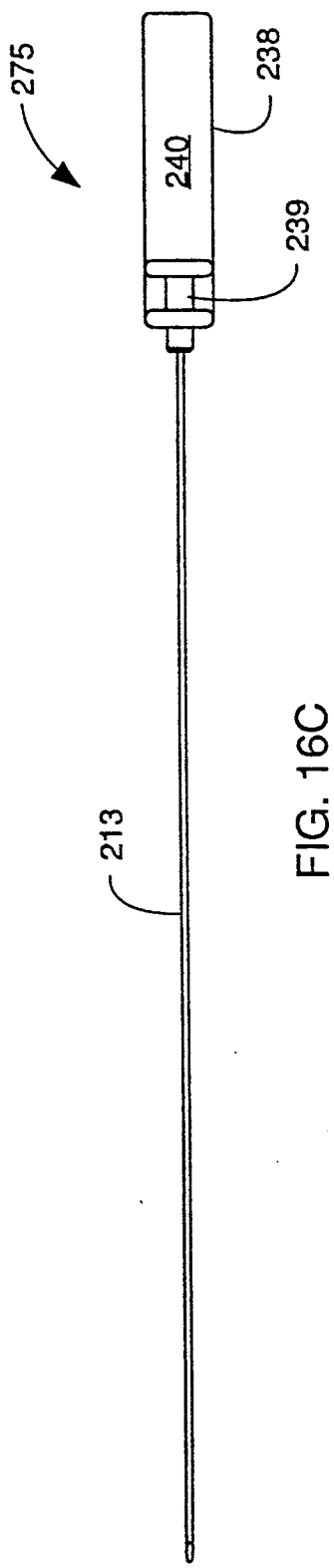
Figure 16E:
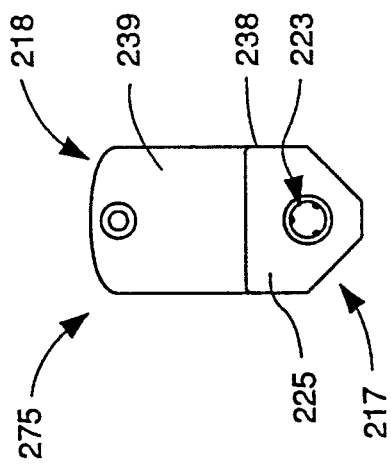
Figure 16D:
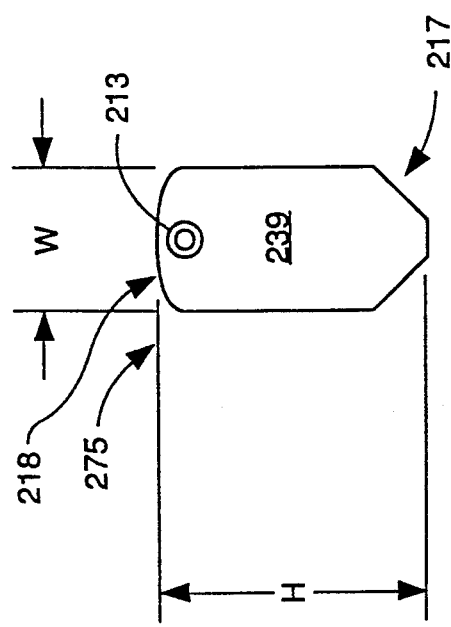
Figure 18A:
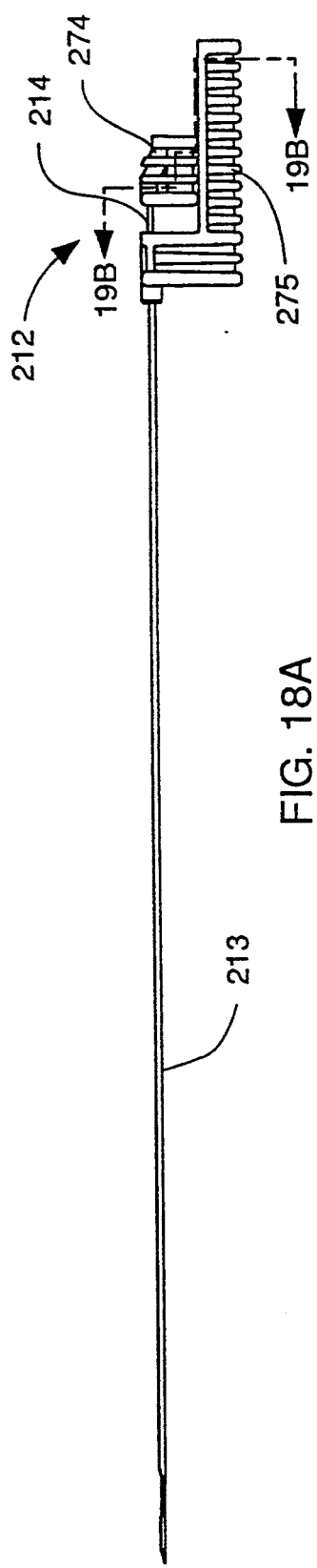
Figure 18B:
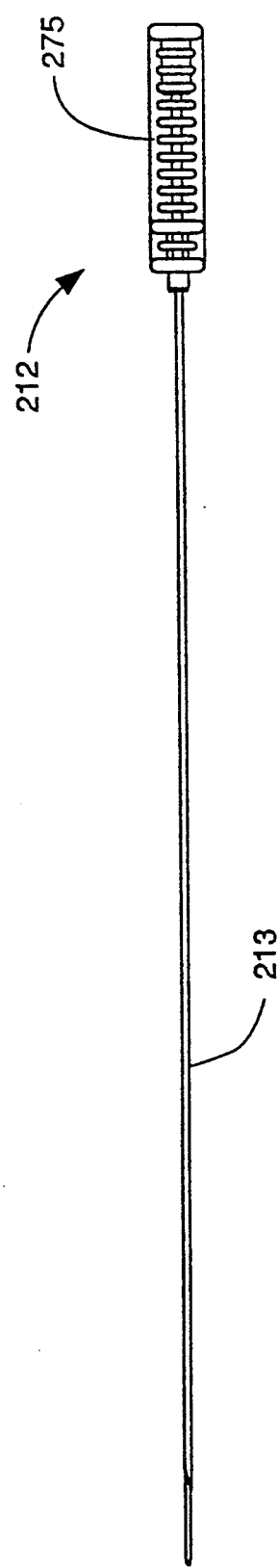
Figure 19A:
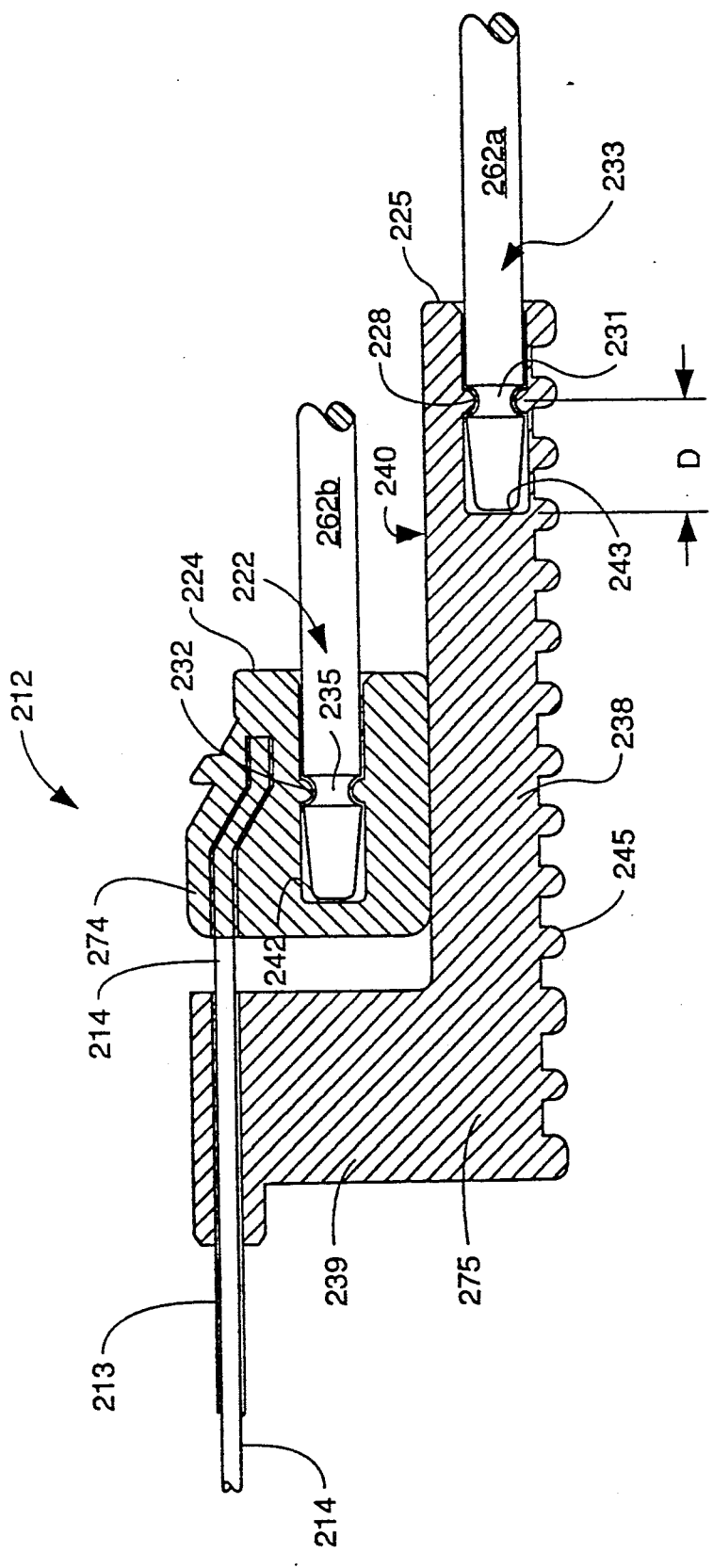
FIG. 19A is a side view in full section of the stylet and cannula assembly according to the present invention shown mounted on two drive pins.
Figure 19B:
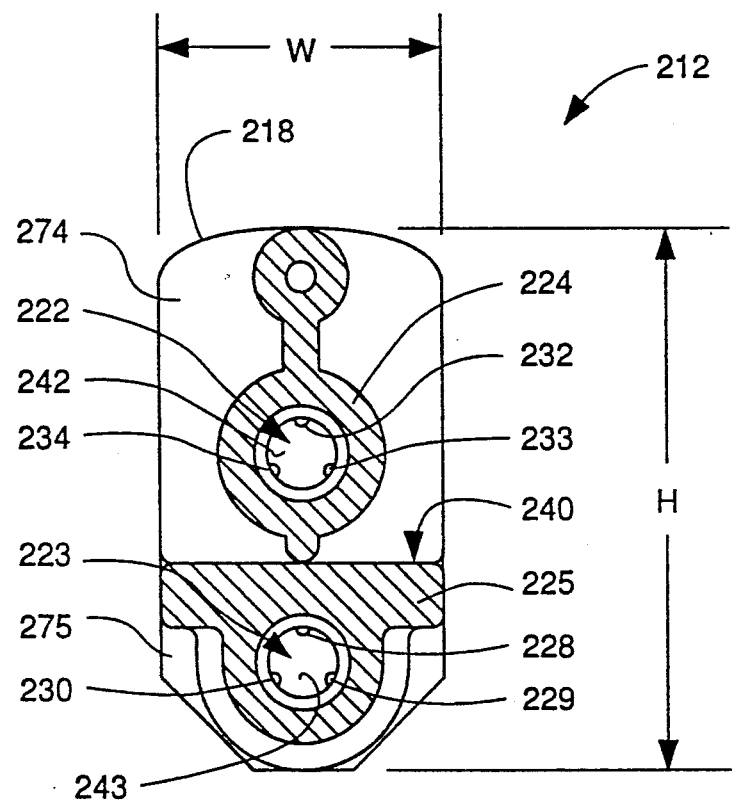
FIG. 19B is a rear cross section view, taken along the line 19B—19B of FIG. 18A.

As illustrated in FIGS. 16D, 18D and 19B, the stylet and cannula assembly 212 has a generally rectangular frontal profile which is receivable in rectangular opening 269 in the front end of the biopsy instrument. This is similar to the previously described rectangular opening 69 sized to accommodate the stylet and cannula mounts 74 and 75 to provide a guide way for the stylet and cannula assembly. Similarly, assembly 212 has a generally rectangular shape having a height "H" and a width "W" as illustrated. In the preferred embodiment, height H is approximately 0.8 inches and width W is approximately 0.4 inches. Note that this generally rectangular shape may vary somewhat, such as with a slightly rounded top profile 218 along the top side of assembly 212 and with truncated corners, such as truncated corner 217 along the bottom side of assembly 212. Opening 269 acts as a guideway in the front end of the biopsy instrument surrounding drive pin 262a and drive pin 262b and keeping the forward and reward movement of assembly 212 in proper alignment.

Mount 274 and mount 275 may have a variety of configurations, such as the use of lateral ribs like rib 244 and rib 245 as illustrated. In the preferred embodiment, mounts 274 and 275 are made of molded plastic, although other materials may be used including metal.

Referring to FIGS. 19A and 19B, a preferred version of a locking mechanism to hold mount 275 and mount 274 on to drive rod 262a and drive rod 262b, respectively, is shown. Drive rod 262a includes annular groove 231 therein near its forward end. Rod 262a is disposed in recess 223. One or more locking projections, such as projection 228, projection 229 and projection 230 engage annular groove 231. These projections are deformable to allow for the projections to snap in and out of the annular groove upon insertion or removal of rod 262a from recess 223. Preferably, these projections are positioned in recess 223 at distance D of at least 0.2 inches behind front wall 243 within recess 223. Distance D may be greater than 0.2 inches if necessary, but should be sufficient to accommodate the tapered forward end of the drive rod. Similarly, in recess 222 of the stylet mount 274, the locking mechanism 232 should be spaced a distance from front wall 242 of at least 0.2 inches. Likewise, drive rod 262b has annular groove 235 therein which receives snap-in locking projections 232, 233 and 234. The locking action caused by the interaction of these projections in the recesses and annular grooves on the drive rods prevent assembly 212 from being shot out of opening 269 like a projectile upon actuation of the drive mechanism in biopsy instrument 210. This allows for a safer instrument while allowing removal by actuation of lever 286, as described above, to overcome the locking action of the projection and grooves. The locking mechanisms also allow for rearward movement of the stylet and cannula in response to rearward movement of the drive rods. It is to be understood that other such locking mechanisms may be utilized including substitution of things such as divots or recesses in the drive rod, rather than annular grooves. Another approach may be the utilization of a recess or groove in the stylet and/or cannula mount with a radially outward projection on the drive rod. Likewise, although a friction fit, such as by utilizing an elastomeric liner may also be used, a positive locking mechanism, as illustrated in preferred.

The present invention also provides the ornamental design for cannula mount 275 and cannula 213, stylet mount 274 and stylet 214, and stylet and cannula assembly 212, as shown and described.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A biopsy stylet and cannula assembly suitable for use with a biopsy instrument having a first drive rod and a second drive rod, comprising:
   a cannula mount having a tubular cannula secured thereto and projecting forwardly therefrom, wherein said cannula mount has first recess means in a back side of said cannula mount receiving a first drive rod of the biopsy instrument therein; and
   a stylet mount having a stylet secured thereto and projecting forwardly within said tubular cannula and slidable with respect to said cannula, wherein said stylet mount has second recess means in a back side of said stylet mount for receiving a second drive rod of the biopsy instrument therein, wherein said first recess means has first locking means for securing to the first drive rod to resist forward removal of said cannula mount from the first drive rod.

2. The stylet and needle assembly of claim 1 wherein the first drive rod has a first annular groove therein and wherein said first locking means comprises means for engaging said first annular groove.

3. The stylet and needle assembly of claim 2 wherein said stylet mount and said cannula mount slide with respect to each other and collectively cooperate to define a generally rectangular frontal profile receivable in a generally rectangular opening acting as a guide way in a front end of the biopsy instrument surrounding the first drive rod and the second drive rod.

4. The stylet and needle assembly of claim 3 wherein said second recess means has second locking means therein for securing to the second drive rod to resist forward removal of said stylet mount from the second drive rod.

5. The stylet and needle assembly of claim 4 wherein the second drive rod has a second annular groove therein and wherein said second locking means comprises means for engaging said second annular groove.

6. The stylet and needle assembly of claim 5 wherein said cannula mount includes a bottom portion and a forward portion, wherein said bottom portion has a top side along which said stylet mount slides, and wherein said forward portion of said cannula mount project above said top side of said bottom portion in front of said stylet mount.

7. The stylet and needle assembly of claim 6 wherein said first recess means in said cannula mount is positioned directly below said second recess means in said stylet mount.

8. The stylet and needle assembly of claim 7 wherein said first locking means comprise at least one radially inward projection with snaps into the first annular groove in the first drive rod, and wherein said second locking means comprise at least one radially inward projection which snaps into the second annular groove in the second drive rod.

9. The stylet and needle assembly of claim 8 wherein said generally rectangular frontal profile defined by said cannula mount and said stylet mount has a vertical height of about 0.8 inches and a horizontal width of about 0.4 inches, and wherein said first locking means is positioned in said first recess means a distance of at least 0.2 inches behind a front wall within said first recess means.

10. The stylet and needle assembly of claim 1 wherein said second recess means has second locking means therein for securing to the second drive rod to resist forward removal of said stylet mount from the second drive rod.

11. The stylet and needle assembly of claim 1 wherein the second drive rod has a second annular groove therein and wherein said second locking means comprises means for engaging said second annular groove.

12. A biopsy stylet and cannula assembly suitable for use with a biopsy instrument having a first drive rod and a second drive rod, comprising:
   a cannula mount having a tubular cannula secured thereto and projecting forwardly therefrom, wherein said cannula mount has first recess means in a back side of said cannula mount for receiving a first drive rod of the biopsy instrument therein; and
   a stylet mount having a stylet secured thereto and projecting forwardly within said tubular cannula and slidable with respect to said cannula, wherein said stylet mount has second recess means in a back side of said stylet mount for receiving a second drive rod of the biopsy instrument therein, wherein said stylet mount and said cannula mount slide with respect to each other and collectively cooperate to define a generally rectangular frontal profile receivable in a generally rectangular opening acting as a guide way in a front end of the biopsy instrument for surrounding the first drive rod and the second drive rod.

13. The stylet and needle assembly of claim 12 wherein said generally rectangular frontal profile defined by said cannula mount and said stylet mount has a vertical height of about 0.8 inches and a horizontal width of about 0.4 inches.

14. A biopsy stylet and cannula assembly suitable for use with a biopsy instrument having a first drive rod and a second drive rod, comprising:
   a cannula mount having a tubular cannula secured thereto and projecting forwardly therefrom, wherein said cannula mount has first recess means in a back side of said cannula mount for receiving a first drive rod of the biopsy instrument therein; and
   a stylet mount having a stylet secured thereto and projecting forwardly within said tubular cannula and slidable with respect to said cannula, wherein said stylet mount has second recess means in a back side of said stylet mount for receiving a second drive rod of the biopsy instrument therein, wherein said cannula mount includes a bottom portion and a forward portion, wherein said bottom portion has a top side along which said stylet mount slides, and wherein said forward portion of said cannula mount projects above said top side of said bottom portion in front of said stylet mount.

15. A biopsy stylet and cannula assembly suitable for use with a biopsy instrument having a first drive rod and second drive rod, comprising:
   a cannula mount having a tubular cannula secured thereto and projecting forwardly therefrom, wherein said cannula mount has first recess means in a back side of said cannula mount for receiving a first drive rod of the biopsy instrument therein; and
   a stylet mount having a stylet secured thereto and projecting forwardly within said tubular cannula and slidable with respect to said cannula, wherein said stylet mount has second recess means in a back side of said stylet mount for receiving a second drive rod of the biopsy instrument therein, wherein the first drive rod and the second drive rod are oriented horizontally, and wherein said first recess means in said cannula mount is positioned directly vertically below said second recess means in said stylet mount.

16. A biopsy instrument, stylet and cannula assembly, comprising:
   a biopsy instrument having a first drive rod and a second drive rod in an opening in a front end of said biopsy instrument;
   a cannula mount having a tubular cannula secured thereto and projecting forwardly therefrom, wherein said cannula mount has first recess means in a back side of said cannula mount sized and positioned for receiving said first drive rod of said biopsy instrument therein;
   a stylet mount having a stylet secured thereto and projecting forwardly within said tubular cannula and slidable with respect to said cannula, wherein said stylet mount has second recess means in a back side of said stylet mount sized and positioned for receiving said second drive rod of said biopsy instrument therein; and
   means for urging said cannula mount and said stylet mount forwardly off of said first drive rod and said second drive rod of said biopsy instrument.

17. The assembly of claim 16 wherein said first recess means has first locking means for securing to said first drive rod to resist forward removal of said cannula mount from said first drive rod, wherein said first drive rod has a first annular groove therein and wherein said first locking means engages said first annular groove, wherein said second recess means has second locking means therein for securing to said second drive rod to resist forward removal of said stylet mount from said second drive rod, and wherein said second drive rod has a second annular groove therein and wherein said second locking means engages said second annular groove.

18. The assembly of claim 17 wherein said means for urging includes a lever on said front end of said biopsy instrument which pivots to urge said cannula mount and said stylet mount forwardly.

19. The assembly of claim 16 wherein said means for urging includes a lever on said front end of said biopsy instrument which pivots to urge said cannula mount and said stylet mount forwardly.

20. A biopsy stylet and cannula assembly suitable for use with a biopsy instrument, comprising:

a cannula mount having a tubular cannula secured thereto and projecting forwardly therefrom, wherein said cannula mount has first recess means in a back side of said cannula mount for receiving a first motor powered cam driven drive rod of the biopsy instrument therein, said first recess means comprising a first recess elongated in an axial direction generally parallel to said cannula to receive said first drive rod past said back side of said cannula mount and within said cannula mount upon axial insertion of said cannula mount through a front side opening of the biopsy instrument for axial loading and axial unloading of the cannula mount through said front side opening; and a stylet mount having a stylet secured thereto and projecting forwardly within said tubular cannula and slidable with respect to said cannula, wherein said stylet mount has second recess means in a back side of said stylet mount for receiving a second motor powered cam driven drive rod of the biopsy instrument therein, said second recess means comprising a second recess elongated in an axial direction generally parallel to said stylet to receive said second drive rod past said back side of said stylet mount and within said stylet mount upon axial insertion of said stylet mount through the front side opening of the biopsy instrument for axial loading and axial unloading of the stylet mount through said front side opening, wherein said stylet mount and said cannula mount collectively cooperate to define a frontal profile axially receivable in said front side opening of said biopsy instrument which acts as a guide way for said cannula mount and stylet mount.

* * * * *

UNITED STATES PATENT AND TRADEMARK OFFICE
CERTIFICATE OF CORRECTION

PATENT NO. : 5,146,921

DATED : September 15, 1992

INVENTOR(S) : Richard A. Terwillinger, John D. Hebert and Jack Hall

It is certified that error appears in the above-identified patent and that said Letters Patent is hereby corrected as shown below:

In Column 1, at Line 40, "Papanicalaou" should read --Papanicolaou--.

In Column 1, at Line 52, "shows: should read --show--.

In Column 1, at Line 56, "devices" should read --device--.

In Column 2, at Line 7, "the" should read --then--.

In Column 4, at Line 33, "is" should read --in--.

In Column 13, at Line 34, "Mount274" should read --Mount 274--.

In Column 14, at Line 66, "project" should read --projects--.

Signed and Sealed this

Sixteenth Day of November, 1993

*Attest:*

BRUCE LEHMAN

*Attesting Officer*        *Commissioner of Patents and Trademarks*